United States Patent
Sullivan et al.

(10) Patent No.: US 7,630,762 B2
(45) Date of Patent: Dec. 8, 2009

(54) MEDICAL DEVICE WITH RESUSCITATION PROMPTS DEPENDING ON ELAPSED TIME

(75) Inventors: Joseph L. Sullivan, Kirkland, WA (US); Fred W. Chapman, Newcastle, WA (US); Daniel W. Piraino, Seattle, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 623 days.

(21) Appl. No.: 11/013,894

(22) Filed: Dec. 15, 2004

(65) Prior Publication Data

US 2006/0129191 A1 Jun. 15, 2006

(51) Int. Cl.
*A61N 1/00* (2006.01)
(52) U.S. Cl. .......................................................... 607/5
(58) Field of Classification Search ................ 607/5–8
See application file for complete search history.

(56) References Cited

U.S. PATENT DOCUMENTS

| | | | |
|---|---|---|---|
| 4,610,254 A | 9/1986 | Morgan et al. | |
| 5,077,667 A | 12/1991 | Brown et al. | |
| 5,334,070 A | 8/1994 | Yu et al. | |
| 5,749,902 A | 5/1998 | Olson et al. | |
| 6,356,785 B1 | 3/2002 | Snyder et al. | |
| 6,438,419 B1 | 8/2002 | Callaway et al. | |
| 7,272,441 B1 * | 9/2007 | Chapman et al. | 607/5 |

OTHER PUBLICATIONS

Lars Wik, Delaying Defibrillation to Give Basic Cardiopulmonary Resuscitation to Patients With Out-of-Hospital Ventricular Fibrillation, JAMA, Mar. 19, 2003, p. 1389-1395, vol. 289, No. 11.
Leonard A. Cobb, Changing Incidence of Out-of-Hospital Ventricular Fibrillation, 1980-2000, JAMA, Dec. 18, 2002, p. 3008-3013, vol. 288, No. 23.
Myron L. Weisfeldt, Resuscitation After Cardiac Arrest, JAMA, Dec. 18, 2002, p. 3035-3038, vol. 288, No. 23.

* cited by examiner

*Primary Examiner*—Mark W Bockelman
(74) *Attorney, Agent, or Firm*—Shumaker & Sieffert, P.A.

(57) ABSTRACT

Methods and apparatus are provided for determining a defibrillation treatment protocol in an external defibrillator using a measurement of elapsed time. The present invention provides a defibrillator with a timer function. Upon activation of the defibrillator, an internal timer begins to run. By closely associating the activation of the defibrillator with the onset of the patient's attack, and by making allowances for inherent time differences between these events, the timer provides a measure of the elapsed time between the onset of the patient's emergency and the presentation of the defibrillator at the patient's side. Using this measure of elapsed time, the defibrillator determines an appropriate treatment therapy, such as CPR or defibrillation therapy.

18 Claims, 5 Drawing Sheets

MEDICAL DEVICE WITH RESUSCITATION PROMPTS DEPENDING ON ELAPSED TIME

FIELD OF THE INVENTION

The present invention generally relates to external defibrillators including Automatic External Defibrillators (AEDs), and more particularly relates to interactive defibrillators having cardiopulmonary resuscitation (CPR) prompts for patient treatment. Still more particularly, the present invention relates to methods of coordinating resuscitation prompts with the time elapsed from the activation of the AED.

BACKGROUND OF THE INVENTION

A normal human heart pumping pattern is called a sinus rhythm, and is regulated by the body's biological pacemaker within the upper right chamber of the heart, which is commonly referred to as the right atrium. This natural pacemaker, which is generally referred to as the sinoatrial (SA) node, sends electrical signals to the right and left ventricular muscles in the lower chambers of the heart. The ventricular muscles then implement the pumping action under control of the SA node. The right ventricular muscle pumps blood to the lungs for oxygenation, and the left ventricular muscle pumps the oxygenated blood to various parts of the body.

In certain circumstances, the normal or sinus heartbeat rhythm may be adversely affected as a result of some type of malfunction in the heart's electrical control system. When this type of malfunction occurs, an irregular heartbeat may result, causing the ventricular muscles to pump ineffectively, thus reducing the amount of blood pumped to the body. This irregular heartbeat is generally referred to as an arrhythmia, which can also lead to Sudden Cardiac Arrest (SCA).

It is estimated that approximately two hundred and twenty-five thousand (225,000) deaths per year are attributable to SCA. A particularly serious type of SCA is known as Ventricular Fibrillation (VF), which is a malfunction characterized by rapid, uncoordinated cardiac movements replacing the normal contractions of the ventricular muscles. In this event, the ventricular muscles are not able to pump blood out of the heart, and there is no initiation of a heartbeat. VF rarely terminates spontaneously, and is therefore a leading cause of sudden cardiac death. The unpredictability of VF and other irregular heat beat conditions exacerbates the problem, and emphasizes the need for early therapeutic intervention to prevent the loss of life.

Defibrillators are devices for providing life-saving electrical shock therapy to persons experiencing an irregular heat beat, such as VF. A defibrillator provides an electrical shock to the heart, in order to convert the irregular heart beat to a normal sinus rhythm. One type of defibrillator is surgically implanted in patients who are considered likely to need electrical shock therapy, precluding the necessity of constant monitoring by medical personnel.

Another commonly used type of defibrillator is the external defibrillator, which sends electrical shock pulses to the patient's heart through external electrodes applied to the patient's chest. External defibrillators may be manually operated, as are typically used in hospitals by medical personnel or may be semi-automatic, semi-automated, fully automatic, or fully automated devices, where they can be used in any location where an unanticipated need may occur. An automatic external defibrillator is commonly referred to as an AED.

It is well known that time is an important factor in the successful application of electrical shock therapy. The survival rate of persons suffering from VF decreases by about ten percent (10%) for each minute the administration of a defibrillation shock is delayed according to some data. It is therefore desirable to minimize the time duration between powering up an external defibrillator and administering the electrical shock therapy to the patient. It is also estimated that the rate of survival for SCA victims averages less than two percent (2%) when defibrillation is delayed ten (10) minutes or more.

In a typical usage of a defibrillator, the defibrillator electrodes are attached to the patient prior to delivery of a defibrillation shock. The defibrillator can also monitor the patient's condition and parameters. This data can be measured and analyzed, and then a defibrillation circuit can be determined based on that analysis. The defibrillator then charges to an appropriate level and applies the shock therapy in a desired format. One or more of these activities can be done by medical/emergency personnel, as in the case of manual defibrillators, or by an automatic or automated process, as in the case of automatic, semi-automatic, automated and semi-automated defibrillators. These actions, while necessary, can also be disadvantageously time-consuming, and can delay the administration of the shock therapy.

Additionally, some defibrillators have been developed that integrate CPR instructions along with shock treatment. CPR is a combination of techniques including artificial respiration (rescue breathing) and artificial circulation (chest compression). One purpose of CPR is to provide oxygenated blood through the body, and to the brain, in those patients where a prolonged loss of circulation places the patient at risk. For example after a period of time without restored circulation, typically within four (4) to six (6) minutes, cells in the human brain can begin to be damaged by lack of oxygen. In some cases, shock therapy does not immediately restore a normal heart rhythm; several shocks may be required. In other cases, CPR should be administered prior to any defibrillation therapy. Thus, different patient conditions may require different combinations of shock therapy and CPR therapy. For example, some patients may only need shock therapy while others may use both shock therapy and CPR. Further, different patients may benefit the combination of CPR and defibrillation in different order. Some may benefit from CPR first, followed by defibrillation; and other different patients may benefit from defibrillation first. It would be desired to develop a defibrillator and defibrillation system that can quickly detect and order a patient's therapy needs.

Many defibrillators also include a CPR protocol. A CPR protocol typically uses voice prompts and/or a form of interactive display, that guides a user in when to apply CPR methods and shock therapy. A CPR-first protocol has been proposed for use with some defibrillation devices. Under this protocol, the defibrillator is configured to prompt CPR therapy as the first type of therapy to be given a patient. In such a device the defibrillator may also include ECG (electrocardiogram) capability in order to monitor patient conditions. One example of an external defibrillator with CPR prompts is described in U.S. Pat. No. 6,356,785. Another is U.S. Pat. No. 6,334,070. The CPR protocol includes prompts which indicate when CPR should be applied. The prompt may be in the form of a visual/graphical display, an audio display, or some other form of communication.

While it is advantageous to integrate CPR and shock therapy, there are instances in which CPR first, prior to shock therapy, is not the appropriate patient treatment. Rather, shock therapy should be administered first, and any delay in doing so is potentially adverse to the patient. Nevertheless, in those systems that have a default CPR-first protocol, it is typical that a user first pass through the CPR prompts in order to reach the shock treatment. Thus, it would be desired to provide a defibrillator that allows for an appropriate selection between a CPR therapy and defibrillation therapy.

Additionally, in those situations in which the defibrillator has been brought to the side of an emergency patient quickly, the small amount of time elapsed generally indicates that defibrillation should first be applied. Thus, time is an important factor in determining a preferred treatment protocol, the time between the onset of the patient attack and the presentation of the defibrillator to the patient. Thus, it would also be desired to provide a defibrillator that can account for the time elapsed between the beginning of a patient emergency and the evaluation of a defibrillator therapy.

Moreover, there are delays inherent in the CPR protocol that may disadvantage certain patients. Algorithms for determining which patients should receive CPR first have several problems. First of all, they require time to acquire the signal (from the patient) and additional time to perform an analysis of the data. This time delays therapy. Although the delay may presumably be small, nevertheless, there are some indications that even small delays can be important for patient treatment.

Secondly, ECG analysis algorithms generally require high-powered CPUs to perform the required analysis in a reasonable amount of time. This adds cost to the product. For some consumers, the added cost may deter the acquisition of a defibrillator as part of the emergency equipment to be kept on hand. Thus, because AEDs are cost-sensitive products, it would be desired to find ways to minimize their cost.

Finally, ECG analysis algorithms have not been shown to work better than a simple timer when it comes to determining whether to perform CPR prior to defibrillation. An estimate of the patient's down time is valuable data that is relatively simply processed for determining whether to perform CPR prior to defibrillation.

Thus, it would be desired to develop a defibrillator with a treatment protocol that takes into account time factors in treatment. For those situations in which only a small amount time has elapsed between the patient suffering an emergency and the presentation of the defibrillator to the patient, the defibrillator can immediately follow a defibrillation protocol without the need to consider CPR treatment.

Hence there exists a need for an improved defibrillator and an improved method for operating a defibrillator. Namely, there is a need for a defibrillator, and especially an external defibrillator, that addresses one or more of the above-noted, and other not explicitly or implicitly mentioned, drawbacks and limitations. It would be desired to provide a defibrillator and a control system thereof that reduces the inherent time delays associated with shock administration in external defibrillators and/or a defibrillator and method of operating a defibrillator that accounts for the time between the onset of a patient emergency and the presentation of defibrillation means to the patient and/or a defibrillator and method of operating the same that uses relatively simple analytic methods involving time in determining a CPR or defibrillation treatment protocol. In addition, it would be desired to provide a defibrillator that includes convenient interactive features so that output and input can be quickly received and supplied by a human operator/user. Finally, it would be desired to provide a defibrillator that, by virtue of the foregoing, offers an improved level of response and patient treatment. The present invention addresses one or more of these needs.

BRIEF SUMMARY OF THE INVENTION

The present invention provides a defibrillator with a timer function. Upon activation of the defibrillator, an internal timer begins to run. By closely associating the activation of the defibrillator with the onset of the patient's attack, and by making allowances for inherent time differences between these events, the timer provides a measure of the elapsed time between the onset of the patient's emergency and the presentation of the defibrillator at the patient's side. Using this measure of elapsed time, the defibrillator determines an appropriate treatment therapy, such as CPR or defibrillation therapy.

In one embodiment, and by way of example only, there is provided a method for determining a defibrillation treatment protocol comprising the steps of: activating a defibrillator; starting a timer within the defibrillator; attaching electrodes of the defibrillator to a patient; sampling the timer to obtain an elapsed time; comparing the elapsed time to a TMIN; ordering a CPR treatment protocol if the elapsed time is greater than the TMIN; and ordering a shock treatment protocol if the elapsed time is less than the TMIN. The method may also comprise the additional steps of performing a shock analysis under the shock treatment protocol; ordering a CPR treatment protocol if shock treatment is not indicated by the shock analysis; and issuing a defibrillation shock if shock treatment is indicated by the shock analysis. The step of activating the defibrillator may include acts such as removing the defibrillator from a wall mount, manually turning on the defibrillator, or receiving a signal (such as a wireless signal or a signal on a data line) from an EMS center. The method may also include sampling the timer a second time to obtain a second elapsed time and then comparing the second elapsed time to the TMIN.

In a further embodiment, and still by way of example, there is also provided an external defibrillator for providing a selected treatment protocol to a patient comprising: a plurality of electrodes affixed to the defibrillator and capable of being attached to a patient so as to provide shock therapy; a plurality of sensing electrodes affixed to the defibrillator and capable of being attached to a patient so as to provide patient data to the defibrillator; an input device disposed on the defibrillator; an output device disposed on the defibrillator; and a controller disposed in the defibrillator, where the controller is coupled to the plurality of electrodes, the plurality of sensing electrodes, the input device, and the output device, and wherein the controller is also configured to: start a timer function upon activation; sense when the sensing electrodes are attached to a patient; sample an elapsed time from the timer function; compare the elapsed time to a set time; order a CPR protocol if the elapsed time is greater than the set time; and order a shock treatment protocol if the elapsed time is less than the set time. The elapsed time may be output through the output device so as to be readable by a human user. Additionally, the defibrillator may include an override function configured within the controller that immediately selects a shock protocol when it is selected. In another feature, the defibrillator controller is further configured so as to sense a patient connection and then to sample an elapsed time upon sensing the patient connection. The defibrillator may also have a power on mode and an automatic power off mode; the timer function may continue to operate for a period of time after the defibrillator passes from power on mode to power off mode. The defibrillator may also include a low power circuit wherein the timer function operates through the low power circuit. The defibrillator may further include non-volatile memory such that the controller is further configured to: record a start time upon activation; store the start time in non-volatile memory; sample a second time; and calculate an elapsed time by comparing the second time with the start time. Also, the defibrillator may include a real-time clock function wherein the start time is recorded by sampling the clock time and wherein the second time is also recorded by sampling the clock time. The defibrillator can also be configured such that the controller senses a patient connection and also senses whether CPR is being administered to the patient; and the controller is further configured to order a shock treatment protocol upon sensing that CPR is being administered to the patient.

Other independent features, characteristics, and advantages of the defibrillator with a timer function will become apparent from the following detailed description, taken in conjunction with the accompanying drawings which illustrate, by way of example, the principles of the invention.

DETAILED DESCRIPTION

The following detailed description of the invention is merely exemplary in nature and is not intended to limit the invention or the application and uses of the invention. Furthermore, there is no intention to be bound by any expressed or implied theory presented in the preceding background of the invention or the following detailed description of the invention. Reference will now be made in detail to exemplary embodiments of the invention, examples of which are illustrated in the accompanying drawings. Wherever possible, the same reference numbers will be used throughout the drawings to refer to the same or like parts.

Figure 1:
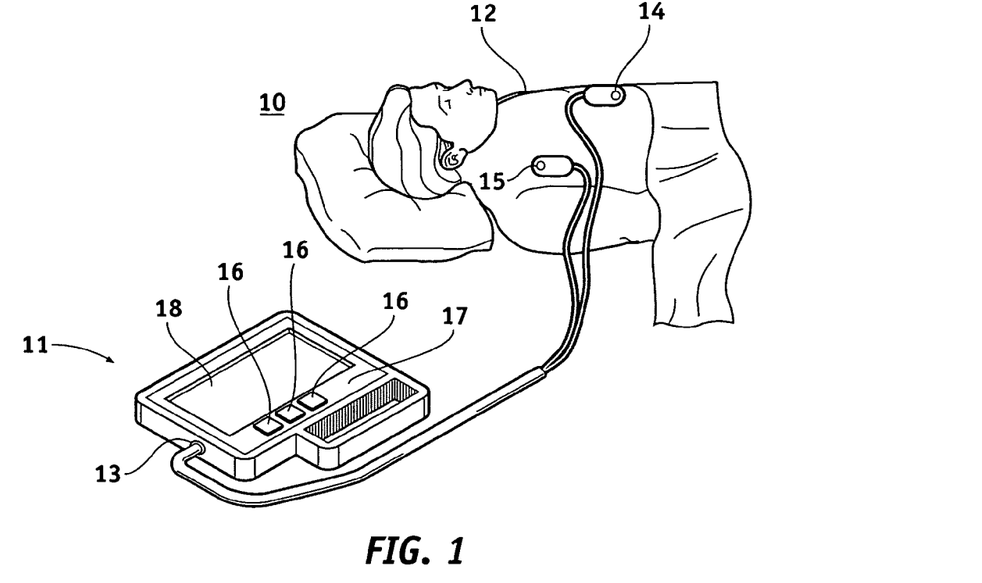
FIG. 1 is an illustration of an external defibrillator system connected to a patient in accordance with an exemplary embodiment of the present invention.

Referring now to FIG. 1 there is shown a typical defibrillator system 10 that may be used in embodiments of the present invention. The system 10 is configured to deliver a defibrillation shock to a patient 12, such as a victim of VF. The defibrillator system 10, includes, but is not limited to, an external defibrillator 11 having a connection port 13 that is configured to receive one or more electrodes (14, 15). (A defibrillator may have more than one connection port). The external defibrillator 11 can be any number of external defibrillators in accordance with the present invention. For example, the external defibrillator 11 can be an Automatic External Defibrillator or Automated External Defibrillator, semi-Automatic or semi-Automated External Defibrillator, or a manually operated external defibrillator. U.S. Pat. No. 4,610,254 to Morgan and U.S. Pat. No. 6,334,070 to Nova provide illustrative examples of defibrillators, and these two patents are hereby incorporated in their entirety by reference.

The external defibrillator 11 preferably includes a user interface 17. The interface 17 may include an output device such as a display 18 that is configured to visually present information which may include various measured or calculated parameters of patient 12 and/or other information to the operator (not shown) of the external defibrillator 11. Display 18 is capable of providing information in textual, numeric, graphical, and/or symbolic format. Information may also be output from the defibrillator through other means such as but not limited to audible signals and/or voice prompts through a speaker or other audio generation device. When a display 18 is included, it may comprise any number of display configurations, e.g., Liquid Crystal Display (LCD) or Active Matrix Liquid Crystal Display (AMLCD). Other output devices are also possible such as LED's and other light indicators. In some embodiments, a printer may also be included for creating hard copies of data. In a preferred embodiment, display 18 provides prompts or instructions to a user related to a treatment protocol. Thus, for example, display 18 may provide CPR instructions and/or shock defibrillation instructions. Display 18 may also provide queries or prompts to input information which are further used in analyzing or selecting a treatment therapy.

The user interface 17 can also include one or more input devices 16 that are configured to receive commands or information from the operator. Input devices may include, but are not limited to, devices such as keys, buttons, switches, touch screens, keyboards, and keypads. The device may also be configured to receive input electronically such as via radio signals, electrical signals, and digital transfer of information. Thus, for example, in some embodiments, the defibrillator receives input from sensing electrodes positioned on patient 12. In one embodiment, the defibrillator is additionally configured to receive input in the form of human voice commands. Thus a receiving device such as a microphone is included, along with the necessary means to convert voice signals to recognizable controller commands. In a preferred embodiment, input devices 16 include antennas and other equipment necessary to receive wireless communication as well as connections so as to receive data lines for the transfer of information.

Electrodes 14, 15 are typically multifunction electrodes in that they are configured both to provide defibrillation therapy and to sense one or more physiology and/or physical parameters of the patient 12 that are received by the external defibrillator 11 at the connection port 13. This is a typical configuration in an AED type device; it will be understood by those skilled in the art that electrodes may be designed differently for different machines. Other defibrillators, including for example manual defibrillators, may also have an additional set of electrodes (not shown), in addition to the multifunction electrodes, used to receive ECG information. These additional electrodes, ECG electrodes, are generally smaller than therapeutic/multifunction electrodes, and ECG electrodes typically plug into a separate port (not shown) than the therapeutic/multifunction electrodes. As is understood in the art, ECG electrodes typically have a three wire lead, though other arrangements are possible. The signals provided by the one more electrodes (14,15) are preferably evaluated by the external defibrillator 11 to determine, among other things, whether a defibrillation shock should be applied to patient 12 in accordance with techniques known to those of ordinary skill in the art. This external defibrillator 11 can, in some embodiments, also evaluate the signals provided by the one more electrodes (14, 15) to determine the waveform parameters of the defibrillation shock (e.g., sinusoidal, monophasic, biphasic, truncated) as well as magnitude and duration; AEDs often include a preprogrammed energy protocol. As is understood in the art, manual defibrillators may allow for a manual selection of shock parameters.

A variety of physiological data and signals of the patient 12 can be sensed by the defibrillator. For example, conventional phonocardiogram (PCG) transducers can be used to convert acoustical energy of the patient's heart to electrical energy for production of a PCG waveform. Additionally, electrical activity of the patient's heart can be converted for production of an electrocardiogram (ECG) waveform. Transthoracic impedance and other physiology signals of the patient may also be detected. This data represented by this information can be collected and processed in the controller of the defibrillator.

Figure 2:
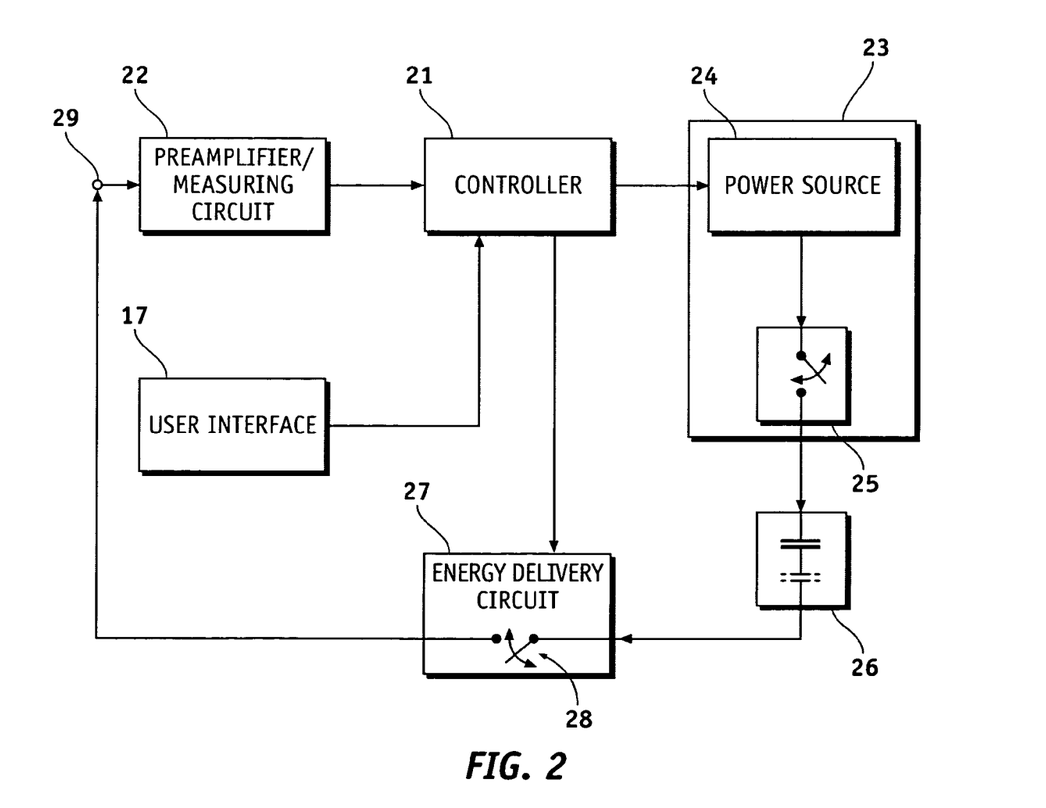
FIG. 2 is a simplified block diagram of an external defibrillator system in accordance with an exemplary embodiment of the present invention.

Referring to FIG. 2, a simplified block diagram of the external defibrillator 11 is illustrated in accordance with an exemplary embodiment of the present invention. The external defibrillator 21 preferably includes a controller 21, the user interface 17 (e.g., switches or buttons 16 and/or display 18 as shown in FIG. 1), a pre-amplifier/measuring circuit 22, a charging mechanism 23 that can include a power source 24 and a switch 25 to couple the power source 24 to the one or more energy storage devices (e.g., capacitors) 26 and an energy delivery circuit 27, which is illustrated as a switch 28 that is configured to selectively couple the one or more energy storage devices 26 to the connection port 29 under the control of the controller 21. The energy delivery circuit 27 can be implemented with any number of circuit configurations. For example, in a biphasic circuit, an H-bridge circuit can be used in accordance with the present invention. The controller 21 can be a single processing unit or multiple processing units and can be implemented with software, hardware, or a combination of hardware and software. The controller 21 is configured to at least partially control the operation of the external defibrillator 11, including control of charging the one or more energy storage devices 26. Controller 21 further controls input and output to the device, including display methods, and any sequencing of queries and responses.

An AED is generally designed for use by a "first responder," a user who would typically be the first person to arrive on the scene of a medical emergency. A first responder may be a layperson with minimal or no AED training. AEDs are being made to be interactive so as to be able to provide a level of guidance to a first responder. This has been found particularly useful with those devices designed for use by laypersons, or others with minimal emergency response training.

It has now been discovered that a defibrillator, including particularly external defibrillators and AEDs, can be configured to include a timer function. The timer function calculates an elapsed time that provides a close approximation of the time between the onset of a patient emergency and the presentation of the defibrillator at the patient's side ready for service. The defibrillator uses this time information, in whole or part, to determine a treatment therapy.

Figure 3:
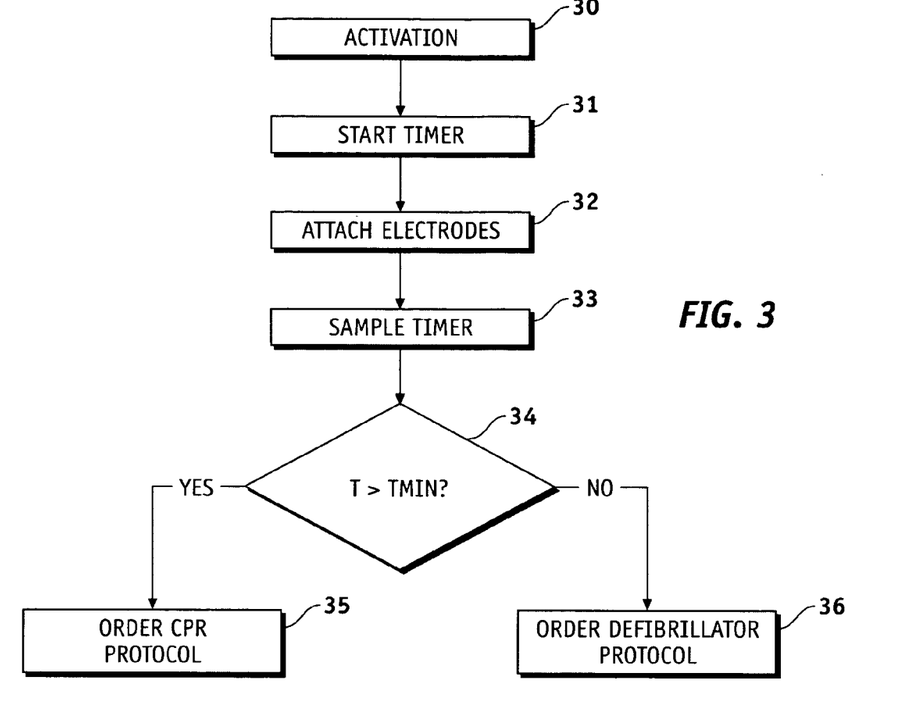
FIG. 3 is a simplified flow chart showing a first exemplary embodiment of a protocol selection method using a timer input configured in an external defibrillator.

Referring now to FIG. 3 there is shown a simplified flow chart which illustrates a first exemplary embodiment of a defibrillator with a timer sensitive treatment selection. The steps shown in the embodiment would preferably be configured into the controller of a defibrillator. The flowchart of FIG. 3 represents a simplified embodiment, and as will be further elaborated, various additional steps, modification, and/or alternate configurations may be added to this process.

In a first step 30, the device is activated. This activation can be done in a number of ways, some described in more detail below. In this embodiment, the activation is as simple as powering or turning on the device. Thus a device may have a power on and power off states or modes.

Once the defibrillator is activated, a timer begins, step 31. The timer records elapsed time beginning with the defibrillator activation. The timer records time through a timer function, which is known in the art. A timer function is a program, or controller configuration, that measures time, in this case from a start point. An electronic clock or timer may be included in the timer function. Values of elapsed time are able to be sampled for use in other routines of the system. A preferred embodiment of the timer function measure up time, elapsed time beginning from a starting point. The timer function may also be configured to be a down counter which begins with a starting value and counts down to zero. Thus, where actions are described herein as being triggered upon reaching a time value, it will be understood that that may be either a positive time value reached through an up counter or a zero (or other) time value reached through a down counter.

As the defibrillator is further used, it is brought to a patient. Eventually, the electrodes of the defibrillator are then attached to the patient, step 32. At this point the defibrillator begins receiving information from the patient, through the electrodes. Also, at this point, the defibrillator (or more particularly, the processor thereof) begins to analyze information and may suggest a treatment protocol.

After electrodes are attached to the patient, the defibrillator samples the timer, step 33. That is, the current elapsed time as measured by the timer (initiated in step 31) is input or read into the controller. That data point, the elapsed time, is then subjected to a query in step 34. It is determined whether the elapsed time is greater than or less than (or also equal to) some set time, TMIN. If the elapsed time is greater than TMIN, then the defibrillator orders a CPR protocol. If the elapsed time is less than TMIN, a defibrillation protocol is ordered. (Cases in which TMIN is equal to the elapsed time may be set to follow one or the other protocols.)

In a further embodiment, the defibrillator may prompt the timer sampling, step 33, once the defibrillator senses it is attached to the patient. The patient connection can be sensed via one of several known methods including receiving data through the defibrillation electrodes, the ECG electrodes, a pulse oximetery probe, a blood pressure cuff, or a pulse detection sensor.

In one embodiment, the clock can be stopped once the electrodes are attached to the patient in step 32. The single clock reading that occurs at that time dictates the sequence of treatment protocols that the defibrillator prompts at that point. However, in another embodiment the timer is not stopped; rather after a time sampling, step 33, the timer continues to run. Additional time samples can be taken at future points to provide additional time information used in making treatment protocol decisions. Thus, for example, when the defibrillator continues to take time samples, once the time sample is greater than TMIN, the defibrillator then orders a CPR protocol rather than a defibrillation protocol. Also, in another embodiment, time samples, along with data taken from the patient, drive routines that indicate a treatment protocol.

Figure 4:
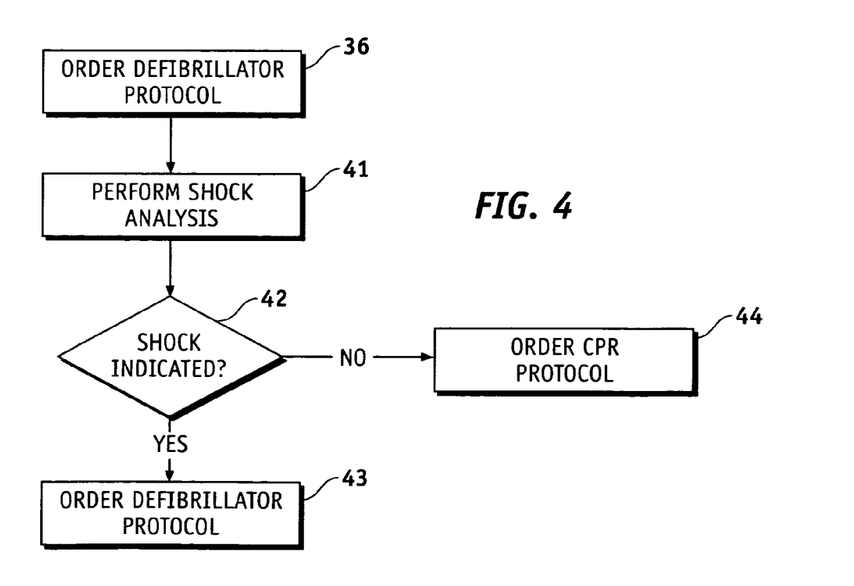
FIG. 4 is a simplified flow chart showing an embodiment of cooperation between a CPR treatment protocol and a defibrillation treatment protocol.

As is understood in the art, the individual treatment protocols, the CPR protocol of step 35 and the defibrillation protocol of step 36, may themselves comprise a number of steps. Further, each of the defibrillation protocol and CPR protocol may cooperate with each other. Referring now to FIG. 4 there is shown a flow chart that describes one embodiment of an interaction between a defibrillation protocol and a CPR protocol. This flowchart begins with step 36 from FIG. 3; there a defibrillation protocol has been selected and ordered by the defibrillator. In the defibrillation protocol there follows a next step of performing an analysis of the patient's ECG to determine if a defibrillating shock should be delivered (referred to as "shock analysis" in this document), step 41. Based on data received from the patient, the defibrillator runs algorithms to determine whether defibrillation therapy is warranted, step 42. If a defibrillation is indicated by that analysis, in a next step the defibrillator administers defibrillation therapy, step 43. There may then follow a further analysis which indicates additional defibrillation therapy, or perhaps CPR therapy. If, however, the initial shock analysis, step 42, does not indicate that defibrillation therapy is warranted, then the system will revert to the CPR protocol, step 44. The CPR protocols typically include a set of prompts or instructions (output) that communicate with a user to perform steps such as heart massage (chest compression) or artificial respiration (rescue breathing) for a number of repetitions and for a certain length of time. Further step 43, the step in which defibrillation therapy is administered, may also include sub-steps of determining the appropriate level and form of defibrillation therapy as described before.

As was previously stated, various configurations of a defibrillator can be integrated with the defibrillator process shown in FIG. 3. For example, the activation step, step 30, may be initiated or otherwise may take place, in various ways. In one embodiment, a defibrillator is manually activated for example by depressing a switch.

In another embodiment, a defibrillator is a wall mounted defibrillator. The defibrillator may be configured so that the act of pulling the defibrillator from the wall is the initiation step. Thus, the timer would begin to run from the first user contact with the device, typically an early moment during an emergency. By linking the timer with wall removal, the timer better approximates an actual elapsed time from the first moment of the emergency. The physical act of removing the defibrillator from the wall may also be linked to a depressing of some button or the completion/breaking of some circuitry that is part of the defibrillator so as to power on or activate the defibrillator. It would be within the level of skill in the defibrillator art to devise a means that links the act of pulling a defibrillator from the wall to an activation of the device.

While a wall mount is a typical placement for an AED, other locations are also possible, such as storage in a box, kit, or at an emergency station. Thus, an act of removing the AED from its place of rest/storage (other than a wall) may also give rise to activation as in the wall mount scenario. In one alternative, a defibrillator may be provided with a mechanism to detect when the defibrillator is put into motion, and a mechanism to start the timer when that motion is first detected. For example, a motion-sensitive switch could be used to start the timer when the defibrillator is put into motion (by, for example, being picked up by a user) or an accelerometer which would output a signal when the defibrillator starts moving, which in turn starts the time interval measurement. In an alternative embodiment, the timer could be started when a user first touches the defibrillator by incorporating into the defibrillator capacitive touch detection techniques (like those used in touch-activated lamps, for example), microswitches or other techniques and devices well-known to those who design external defibrillation devices. In embodiments such as these, the timer may be started prior to activation of the defibrillator.

In a further embodiment, the activation step, step 30, takes place in conjunction with a call to an emergency service. Again, linking the activation step to the emergency call closely aligns the timer initiation, step 31, to the actual time when the emergency began. Now, the means by which the activation step 30 is linked to the emergency service notification may vary. For example, in one embodiment, an EMS responder may physically activate the defibrillation device upon receiving an emergency notification. However, preferably, there is provided some automatic link between an emergency call and activation of the device 30. In this kind of system a call to an EMS center triggers a signal, and the signal in turn activates the defibrillator. This triggering mechanism can take the form of a wireless radio signal, a hard communication link, or even a computer command, among other forms.

Figure 5:
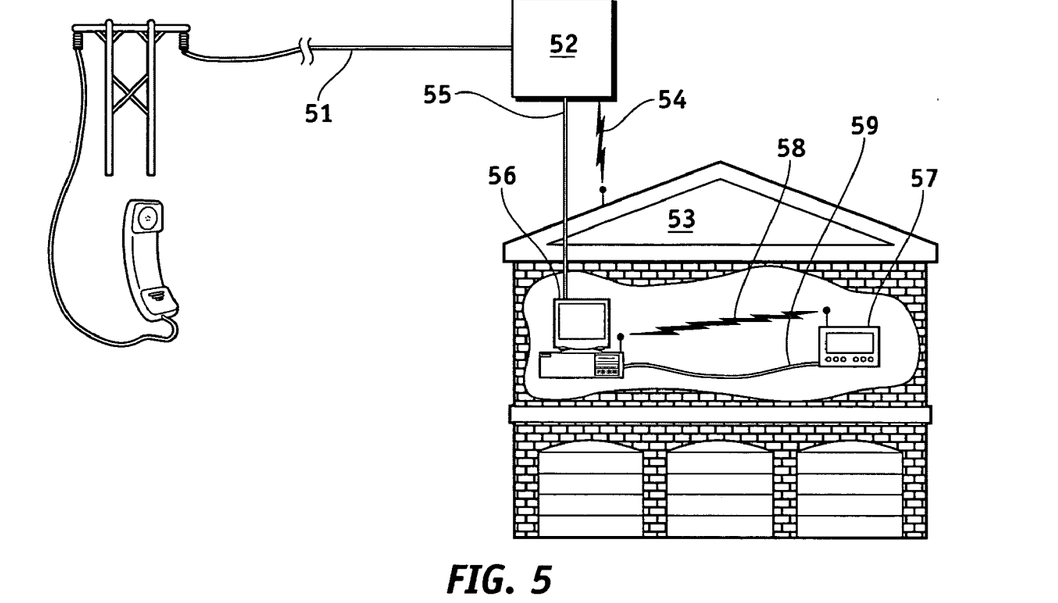
FIG. 5 is a schematic view showing an activation of a defibrillator with a timing function according to an embodiment of the present invention.

Referring now to FIG. 5 there is illustrated an exemplary embodiment of a system that includes an automatic activation feature. An emergency event is first reported by a member of the public by a call over a phone line 51. The emergency call is made to a local emergency responder such as an EMS center 52. A hard line is indicated in the figure, but wireless calls are also to be included therein. The EMS center 52 records the time at which the call is first received along with other emergency information as part of the intake process. The time the call was received will eventually become the start time for the timer function in the defibrillator. Upon receiving information, including the call time, from the caller, the EMS center 52 transmits emergency information to an emergency responder, such as fire station 53. The fire station 53 in this case would be selected by EMS criteria including, for example, the proximity to the patient. The communication link between the EMS center 52 and the fire station 53 may include various means such as, but not limited to, wireless communication 54 or data line 55. Where wireless communication is utilized, enabling means such as hardware, software, antennas and transferring ground lines may not be illustrated. In one preferred embodiment, fire station 53 receives emergency information through a computer 56 that is in turn connected to defibrillator 57. Emergency information received at the fire station includes a signal that is passed on to and activates the defibrillator 57. Within the fire station itself various means may be configured by which to relay an activation signal, along with the start time, to the defibrillator. Two are illustrated, and they include wireless communication 58 and data line 59. An activation command may be relayed to the defibrillator through a wireless signal or through the data line. Alternatively an activation command may be generated by an emergency response computer located in the fire station, or in some other location. In a preferred embodiment, a wireless communication 58 activates a defibrillator 57 located on a vehicle, such as a fire truck or ambulance. In this way, a defibrillator 57 may be prepositioned on the emergency response vehicle and there is thus no delay in retrieving a defibrillator and bringing it to the vehicle. The signal to the defibrillator carries information both to activate the defibrillator and to convey the start time of the emergency. In a further embodiment, an initial time value is downloaded from the dispatch center 52 to defibrillator 57. In this embodiment, the signal transmitted from the EMS center 52 may also include information that provides an initial time value.

It will be appreciated that in emergency situations, the time at which the medical emergency takes place (e.g., the onset of VF) may not correspond precisely with the activation, step 30, of the defibrillator. For a variety of reasons, there may be some delay between these events. Just to list a few, the patient suffering an attack may not be observed or noticed for some time period. Alternatively, where an EMS call is involved, there may be some delay in making that call. Thus, for a number of reasons, it may be desired to adjust the timer function in the defibrillator to account for this inherent delay. There are various ways to allow for such a time adjustment.

In one embodiment, a time adjustment is provided by presetting the TMIN value with some quantity that provides a built-in adjustment. For example, certain medical data indicate that in ideal situations the TMIN value should be set at approximately 5 (five) minutes, i.e., CPR should be applied first when defibrillation capability is brought to a patient more than five minutes from the onset of VF. This is the ideal situation, TMIN=5 min. However, empirical and practical evidence may indicate that there is an average delay of one (1) to two (2) minutes between the onset of VF and the average emergency response. In such a situation the TMIN may be set at three (3) to four (4) minutes to allow for the inherent delay. Of course, other values for the ideal response time as well as the time offset therefrom may be used that differ from the exemplary values discussed in this paragraph.

In another embodiment, the time adjustment is provided, not to TMIN values, but to the timer function. This may include commencing the start timer step, step 31, at some value greater than zero. For example, the start timer step may begin with a start time value of one (1) minute, or some other value. This offset to the start time corresponds with any delay that is desired to be adjusted.

In still another embodiment, the means to provide a time adjustment allows for the user to input an adjustment to the timer function. The defibrillator is configured so as to allow a user to input some value that serves as a time adjustment. In this manner a value can be determined that accounts for a desired time offset. The value may serve as either an adjustment to the TMIN value or to the time recorded by the timer function. The input may be submitted in response to a query or prompt generated by the system. The user may alternatively command the device to accept an adjustment. Various input devices, described above, may be used for making this adjustment. In a different embodiment, the value for TMIN is not preset, rather the TMIN value is input into the defibrillator system. Thus, it is preferred that the defibrillator be programmable with respect to TMIN values. Additionally, where information is provided to the defibrillator through an EMS center, the information transmitted by the EMS center to the defibrillator may include time adjustment information.

Figure 6:
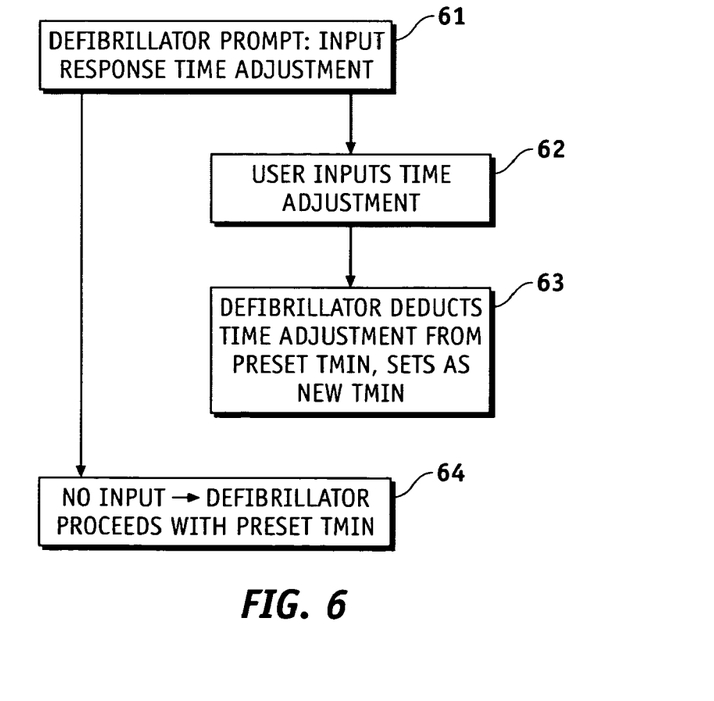
FIG. 6 is a simplified flow chart showing a user input time adjustment to the defibrillator timer function according to an embodiment of the present invention.

An illustration of an embodiment of the programmable time adjustment is illustrated in FIG. 6. In a first step, step 61, the defibrillator issues a prompt that asks for a time adjustment. The prompt may be a graphical output such as "INPUT RESPONSE TIME ADJUSTMENT". If the user responds, he does so in step 62 where a time adjustment is input. The defibrillator receives the input time adjustment, step 63. In this embodiment, the time adjustment amount is deducted from the TMIN value. The system further makes allowance for the situation in which no time adjustment is input. In that event, step 64, the system uses a preset TMIN value.

Still another means for making a time adjustment allows for a time adjustment by virtue of patient data. Once defibrillator electrodes are attached to the patient, the device begins to receive patient data, as is known in the art. Certain data may indicate that the true time from the onset of the medical emergency does not correspond with the time presently measured by the timer function. An appropriate time adjustment may then be automatically input into the system.

Finally, with respect to time adjustments, it is noted that more than one, or even all, of the above-discussed means to make time adjustments may be combined in a single device.

Figure 7:
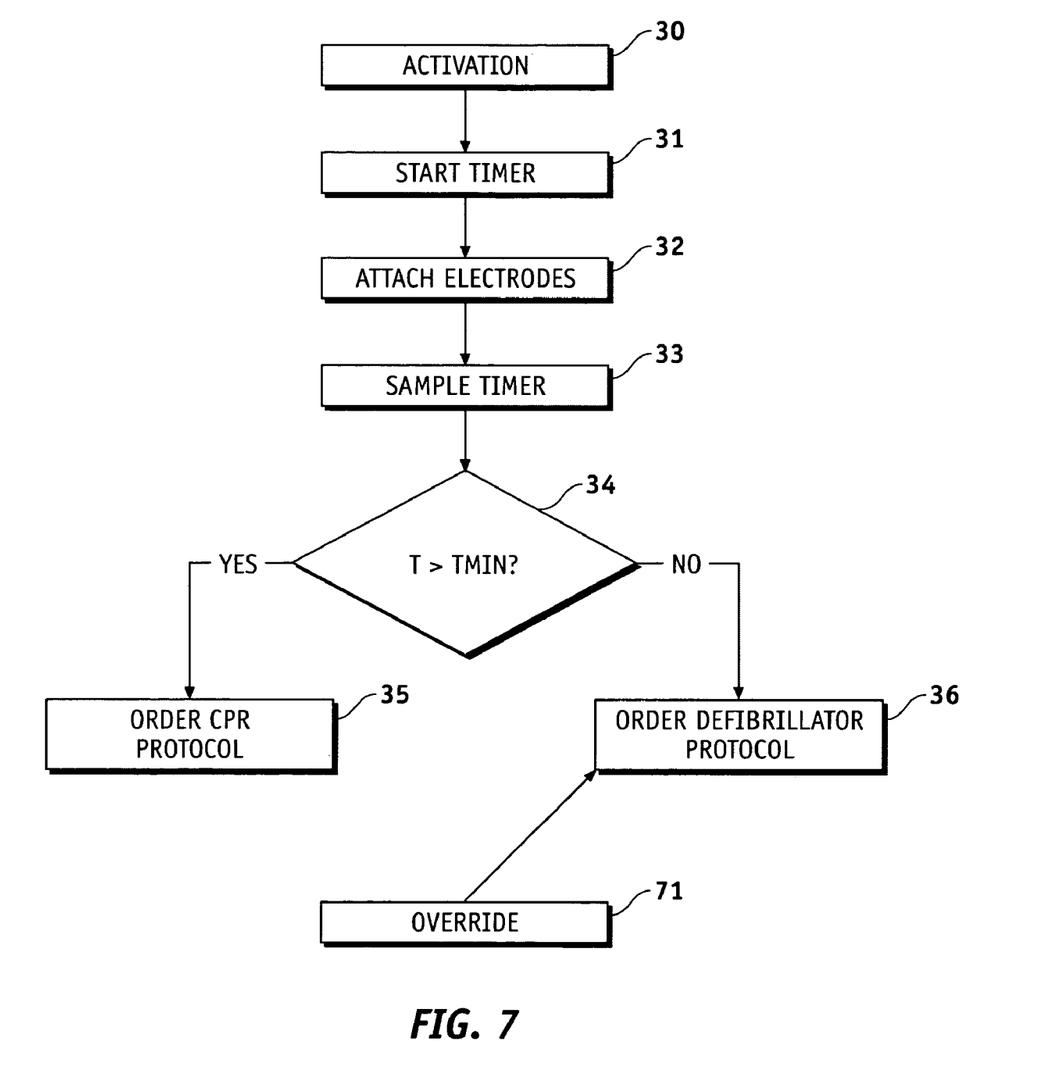
FIG. 7 is a simplified flow chart showing the override function to the defibrillator timer function according to an embodiment of the present invention.

In one embodiment, the timer-based algorithm may be overridden. This may be appropriate where, for example, bystander CPR has been administered to the patient at the time the defibrillator is brought to the patient. Thus, in a preferred embodiment, the defibrillator includes a button or other input device that allows for a user to opt out of the timer-based treatment decision-making routine. FIG. 7 is a flow chart that illustrates the override function. Activating the override input, step 71, orders the controller to proceed directly to a shock treatment protocol, step 36. Further, the defibrillator may automatically override the timer algorithm where it detects that CPR is being applied to a patient when defibrillator connection with the patient is sensed. These embodiments may be useful in those situations where, for example, a first responder without a defibrillator begins to administer CPR to a stricken person. Later, the defibrillator is brought to the emergency scene and is attached to the patient. It is not necessary that the defibrillator determine whether or not a responder should apply CPR because CPR has already been, and is being, administered to the patient. Thus, the defibrillator is commanded to bypass the decision routine, or, the defibrillator senses that CPR is being administered and automatically bypasses the timer routine.

Some AEDs automatically turn off their own power if they are not used within a specific amount of time. And correspondingly, the AED also has a power on and a power off mode. This automatic turn off is typically done in order to avoid unnecessarily draining the batteries. However, such an automatic power-off feature may interfere with the operation of the timer function. In order to avoid inappropriately resetting the response timer due to the power-off feature, an AED should continue to maintain the timer for a period of time even if the remainder of the unit has powered off. In one embodiment, the timer could operate through a low-power circuit that remains active even in the power-off mode. Alternatively, a real-time clock function could be used as part of the timer function. The time of day could be stored in non-volatile memory (which requires little or no power) as a start time when the timer function is started. Later, the elapsed time can be calculated by again sampling the real-time clock and comparing the newly sampled time with the start time. In still another embodiment, the defibrillator could include an activation mode that turns on the response timer function, but allows the remainder of the device to remain powered off. Later, when the device is ready for use with the patient, the remainder of the device may be activated.

While the timer function as described herein has particular use with respect to defibrillators and particularly with defibrillator treatment therapy, the timer function may also be used in other patient care decisions. Mild resuscitative hypothermia has been identified as a therapy that appears to be beneficial for patients with long down times. In addition to having a threshold value for CPR and defibrillation therapy prompts, the defibrillator could also have a threshold time value for hypothermia therapy. A device configured in this manner may provide a prompt for immediate defibrillation if the response time is less than a first time (e.g. five (5) minutes, or approximately four (4) to approximately six (6) minutes), a prompt for CPR first if the response time is more than the first time but less than a second time (e.g. ten (10) minutes, or approximately nine (9) to approximately eleven (11) minutes), and a prompt for hypothermia therapy (or other advanced care) if the time is greater than the second time (e.g. ten (10) minutes). Hypothermia therapy would likely be provided by trained ACLS personnel or by hospital staff.

Figure 8:
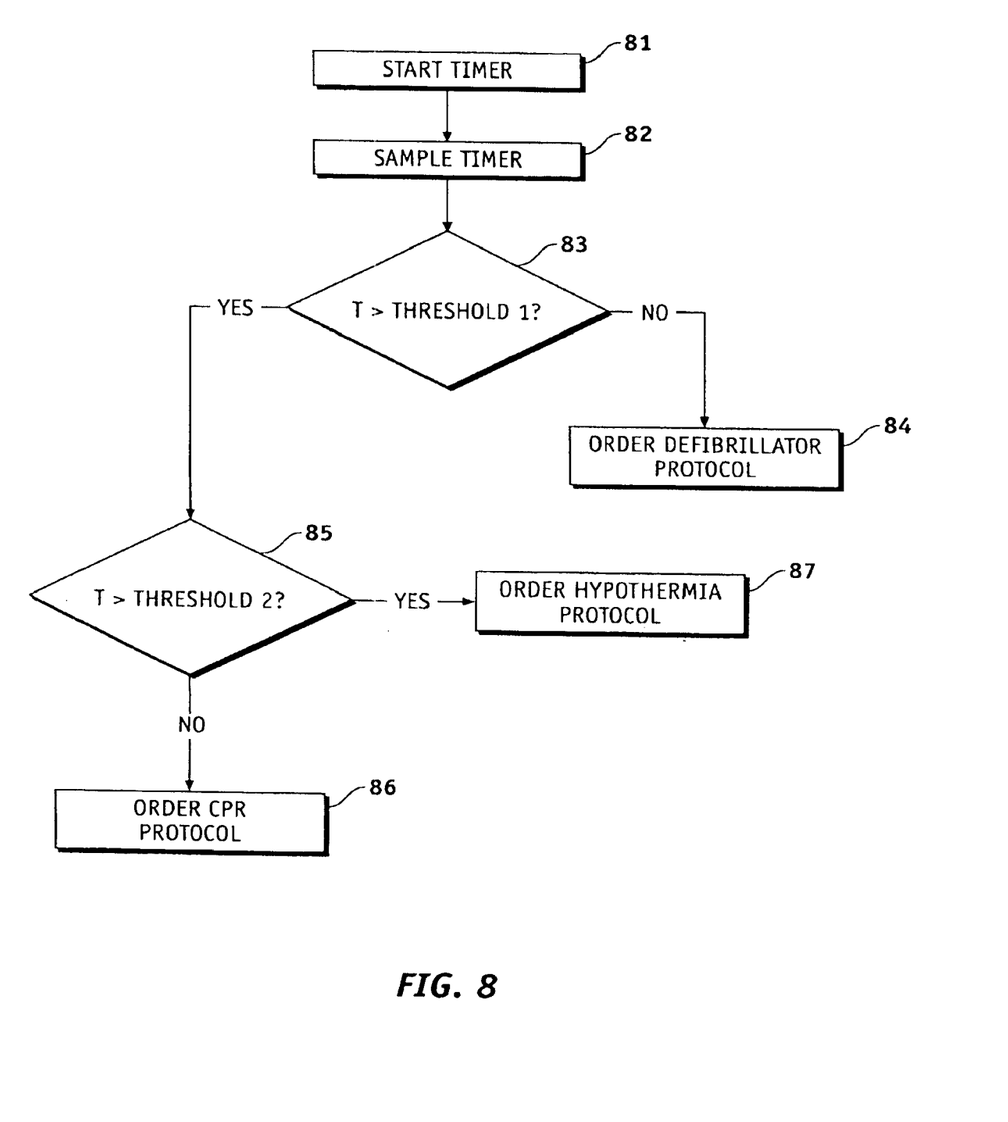
FIG. 8 is a simplified flow chart showing a decision tree for patient therapy configured in a defibrillator that involves three patient therapies and two threshold times, according to an embodiment of the present invention.

There is shown in FIG. 8 a flow chart that illustrates an embodiment of a controller configuration that includes a hypothermia therapy. In a first step a timer is started, step 81, and there follows a sample of the timer, step 82. (Various steps involving activating the defibrillator and attaching electrodes to the patient are omitted.) The sampled time is compared to a first threshold time, step 83. If the sampled time is less, a defibrillation protocol is ordered, step 84. If the sampled time is greater, a second test (step 85) is performed. There, the sampled time is compared to a second threshold time. If the sampled time is less than the second threshold time, a CPR protocol is ordered, step 86. If, however, the sampled time is greater than the second threshold time, a hypothermia protocol is ordered, step 87. As before, cases in which the sampled time is equal to a threshold time may be treated following one or the other of the options.

Still another emergency treatment decision involves rescue breathing. Some medical research suggests that patients who have been in cardiac arrest for a relatively short duration receive relatively little benefit from rescue breathing therapy. Thus, while performing CPR on these patients the caregiver would perform only chest compressions. Eventually, if circulation and spontaneous breathing is not restored, rescue breathing should be done. The timer function can be used to provide appropriate prompts and indications to the caregiver so that he performs the proper proportion of breaths and chest compressions. The resuscitation timer would have a threshold value that would determine whether it is appropriate to perform chest compressions only or to do breaths as well. Still another emergency medical treatment decision involves duration of CPR. AEDs normally have a particular time duration (X) for CPR programmed into them (or sometimes two CPR duration lengths, X and Y). In some devices, these CPR duration lengths are implemented via voice prompts to instruct the rescuer to provide X seconds of CPR after a "no shock advised" prompt or Y seconds of CPR after delivery of the last shock in a stack of shocks. In the case of a patient who has been down for an elapsed time greater than some threshold, it may be desirable to set the CPR duration to be longer than otherwise would be the case. For example, a device that would nominally deliver prompts aiming to provider 60 seconds of CPR after a "shock advised" decision, would issue prompts aimed to provide for 90 seconds when the elapsed time is greater than a first threshold value T1 but less than a second threshold value T2, and 120 seconds when the elapsed time is greater than a second threshold value T2, where T1<T2. The 90 second and 120 second CPR durations are examples only. Other durations, such as, for example, 120 seconds for elapsed time>T1 (but less than T2), and 180 seconds for elapsed time>T2. Elapsed time may also be used in making a decision on whether to prompt for a pulse check in some circumstances. The prompt for pulse check could be eliminated in appropriate cases where the elapsed time since onset of the patient's emergency condition results in a situation where a pulse check will be of little to no benefit to the patient, but would delay subsequent steps in the treatment protocol. In such cases, the elapsed time measurement can be used to decide whether to eliminate the prompt for pulse check in a specific rescue situation.

Still another emergency treatment decision involves administration of drugs to the patient. Some drugs would be helpful to a patient who has been in cardiac arrest for a relatively long time, but would be far less helpful if the time since onset of cardiac arrest has been relatively short (or vice versa). For patients who have been in an emergency condition such as cardiac arrest a very long time, aggressive drug therapy may be more appropriate than it would be for another patient who has been in the condition for a shorter time period. Decisions on whether and how to administer drugs such as epinephrine, vasopressin or amiodarone may be modified based on elapsed time since onset of the patient's emergency condition. Long down-time patients may benefit from drug application before or simultaneous with defibrillation therapy.

In view of the foregoing, it should be appreciated that methods and apparatus are available that allow a defibrillator to be configured such that a timer function records a time between the activation of the defibrillator at the onset of an emergency and the disposition of the defibrillator at the patient's side. The defibrillator may use the timer function to determine an optimal patient therapy. While a finite number of exemplary embodiments have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing exemplary embodiments of the invention. It being understood that various changes may be made in the function and arrangement of elements described in an exemplary embodiment without departing from the scope of the invention as set forth in the appended claims.

What is claimed is:

1. An external defibrillator for providing a selected treatment protocol to a patient comprising:
    at least one connection port disposed on the defibrillator capable of connecting with a plurality of electrodes, the electrodes being capable of being attached to a patient so as to provide patient data to the defibrillator;
    an input device disposed on the defibrillator;
    an output device disposed on the defibrillator; and
    a controller disposed in said defibrillator, said controller coupled to said connection port, said input device, and said output device, and wherein said controller is also configured to:
        receive an activation command from an emergency medical service (EMS) center;
        start a timer function upon receiving the activation command;
        sample an elapsed time from the timer function;
        compare the elapsed time to a set time;
        order a CPR protocol if the elapsed time is greater than the set time; and
        order a shock treatment protocol if the elapsed time is less than the set time.

2. The defibrillator according to claim 1 wherein said elapsed time is output through the output device so as to be readable by a human user.

3. The defibrillator according to claim 1 further comprising an override function configured within said controller that immediately selects a shock treatment protocol when selected.

4. The defibrillator according to claim 1 wherein the controller is further configured so as to sense a patient connection and sample an elapsed time upon sensing the patient connection.

5. The defibrillator according to claim 1 wherein said defibrillator has a power on mode and an automatic power off mode, and wherein said timer function continues to operate for a period of time after the defibrillator passes from power on mode to power off mode.

6. The defibrillator according to claim 1 further comprising a low power circuit and wherein the timer function operates through the low power circuit.

7. The defibrillator according to claim 6 wherein said defibrillator has a power off and power on mode, and wherein said low power circuit remains active in power off mode.

8. The defibrillator according to claim 1 wherein said defibrillator further comprises non-volatile memory and wherein said controller is further configured to:
   record a start time upon activation;
   store the start time in non-volatile memory;
   sample a second time; and
   calculate the elapsed time by comparing the second time with the start time.

9. The defibrillator according to claim 8 wherein said defibrillator further comprises a real-time clock function and wherein the start time is recorded by sampling the clock time and wherein the second time is also recorded by sampling the clock time.

10. The defibrillator according to claim 1 wherein the controller is further configured so as to sense a patient connection and to sense whether CPR is being administered to the patient; and wherein the controller is further configured to order a shock treatment protocol upon sensing that CPR is being administered to the patient.

11. The defibrillator according to claim 1 wherein the controller is further configured so as to allow a user to bypass the configuration wherein an elapsed time is sampled, the elapsed time is compared to a set time, and a CPR protocol is ordered, by ordering the controller to proceed directly to order the shock treatment protocol.

12. The defibrillator according to claim 1, wherein the activation command received from the EMS center is a wireless signal.

13. The defibrillator according to claim 1, wherein the activation command received from the EMS center is a signal transmitted over a data line.

14. The defibrillator according to claim 1, wherein the activation command is generated by an emergency response computer.

15. The defibrillator according to claim 1, wherein a fire station relays the activation command from the EMS center to the defibrillator.

16. The defibrillator according to claim 1, wherein the activation command contains information relating to an initial time value for the timer function.

17. The defibrillator according to claim 16, wherein the initial time value is a time at which the EMS center received a call.

18. The defibrillator according to claim 1, wherein, when the shock treatment protocol is ordered, the controller is further configured to:
   perform a shock analysis;
   order a CPR treatment protocol if shock treatment is not indicated by the shock analysis; and
   issue a defibrillation shock if shock treatment is indicated by the shock analysis.

* * * * *

UNITED STATES PATENT AND TRADEMARK OFFICE
CERTIFICATE OF CORRECTION

PATENT NO. : 7,630,762 B2
APPLICATION NO. : 11/013894
DATED : December 8, 2009
INVENTOR(S) : Sullivan et al.

It is certified that error appears in the above-identified patent and that said Letters Patent is hereby corrected as shown below:

Column 13

Line 46, "shock advised" should read --no shock advised--

Column 13

Line 45, "provider" should read --provide--

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

PATENT NO.         : 7,630,762 B2                                       Page 1 of 1
APPLICATION NO. : 11/013894
DATED              : December 8, 2009
INVENTOR(S)        : Sullivan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1291 days.

Signed and Sealed this

Twenty-first Day of December, 2010

David J. Kappos
*Director of the United States Patent and Trademark Office*